US010024442B2

(12) United States Patent
Maenz et al.

(10) Patent No.: US 10,024,442 B2
(45) Date of Patent: Jul. 17, 2018

(54) VALVE FOR A DIALYSIS MACHINE AND DIALYSIS MACHINE

(71) Applicant: B. BRAUN AVITUM AG, Melsungen (DE)

(72) Inventors: Peter Maenz, Melsungen (DE); André Wagner, Kassel (DE); Katharine Felski, Melsungen (DE); Rudolf Roessler, Spangenberg (DE); Martin Riemann, Alheim (DE); Bjoern Broeker, Staufenberg (DE); Tibor Osztódi, Budapest (HU)

(73) Assignee: B. BRAUN AVITUM AG, Melsungen (DE)

( * ) Notice: Subject to any disclaimer, the term of this patent is extended or adjusted under 35 U.S.C. 154(b) by 374 days.

(21) Appl. No.: 14/790,232

(22) Filed: Jul. 2, 2015

(65) Prior Publication Data
US 2016/0010755 A1 Jan. 14, 2016

(30) Foreign Application Priority Data
Jul. 9, 2014 (DE) .......................... 10 2014 109 639

(51) Int. Cl.
*F16K 7/12* (2006.01)
*F16K 47/04* (2006.01)
(Continued)

(52) U.S. Cl.
CPC ................. *F16K 7/12* (2013.01); *A61M 1/14* (2013.01); *A61M 39/227* (2013.01);
(Continued)

(58) Field of Classification Search
CPC ................. A61M 1/14; A61M 1/1635; A61M 2039/2406; A61M 2039/246;
(Continued)

(56) References Cited

U.S. PATENT DOCUMENTS

| 5,009,775 A | 4/1991 | Tsuji et al. |
| 5,267,964 A | 12/1993 | Karg |

(Continued)

FOREIGN PATENT DOCUMENTS

| CN | 1398194 A | 2/2003 |
| CN | 205127126 U | 4/2016 |

(Continued)

OTHER PUBLICATIONS

European Search Report with translation for EP 15172872 dated Nov. 10, 2015.

(Continued)

*Primary Examiner* — John Kim
(74) *Attorney, Agent, or Firm* — RatnerPrestia (57) ABSTRACT

A pressure compensation valve for a dialysis machine is disclosed. The pressure compensation valve has a valve housing, in which a flow path with fresh dialysate is separated from a flow path with exhausted dialysate by a diaphragm. The diaphragm and the valve housing are configured such that pressure compensation is possible. In addition, the diaphragm is configured such that no vibrations or a reduced amount of vibrations and/or no noise emission or a reduced amount of noise emission will occur during operation. Furthermore, a dialysis machine comprising such a pressure compensation valve is disclosed. The dialysis machine comprises a balancing unit, and the pressure compensation valve is arranged on the outlet side of the balancing unit.

13 Claims, 4 Drawing Sheets

(51) Int. Cl.
*A61M 39/22* (2006.01)
*A61M 39/24* (2006.01)
*A61M 1/14* (2006.01)
*A61M 1/16* (2006.01)

(52) U.S. Cl.
CPC ............. *A61M 39/24* (2013.01); *F16K 47/04* (2013.01); *A61M 1/1635* (2014.02); *A61M 2039/2406* (2013.01); *A61M 2039/246* (2013.01); *A61M 2205/42* (2013.01)

(58) Field of Classification Search
CPC ............ A61M 2205/42; A61M 39/227; A61M 39/24; F16K 47/04; F16K 7/12

See application file for complete search history.

(56) References Cited

U.S. PATENT DOCUMENTS 6,220,299 B1 4/2001 Arvidsson et al.
6,471,855 B1 10/2002 Odak et al.

FOREIGN PATENT DOCUMENTS

| | | |
|---|---|---|
| DE | 693 28 271 | 12/2000 |
| DE | 698 19 715 | 4/2004 |
| EP | 0 597 817 | 5/1994 |
| JP | H05 146506 | 6/1993 |
| WO | WO 02/056992 | 7/2002 |
| WO | WO 2009/055639 | 4/2009 |

OTHER PUBLICATIONS

German Search Report for DE 10 2014 109 639.8 dated Feb. 9, 2015.
Chinese Office Action for Chinese Application No. 201510398171.9, dated Dec. 18, 2017 with translation, 10 pages.

VALVE FOR A DIALYSIS MACHINE AND DIALYSIS MACHINE

CROSS REFERENCE TO RELATED APPLICATIONS

This application claims priority to German application DE 10 2014 109 639.8 filed Jul. 9, 2014, the contents of such application being incorporated by reference herein.

FIELD OF THE INVENTION

The present invention starts from a valve, in particular a pressure compensation valve, for a dialysis machine. In addition, the invention relates to a dialysis machine comprising this kind of valve.

DESCRIPTION OF THE RELATED ART

EP 0 597 817 discloses such a dialysis machine. Fresh dialysate is here conveyed via a pump from a dialysate source to a dialyzer. From the dialyzer, exhausted dialysate flows to a dialysate sink. In order to allow fresh and exhausted dialysate to be balanced, a balancing unit is provided. This balancing unit comprises first and second balancing chambers. Each of the balancing chambers has arranged therein a flexible diaphragm, which separates two cells from one another. Making use of switching valves, the first cells of the balancing chambers can, independently of one another, be supplied with fresh dialysate and fresh dialysate can be discharged therefrom. The second cells of the balancing chambers, however, can be supplied, independently of one another, with exhausted dialysate via switching valves and exhausted dialysate can be discharged therefrom. For equalizing the pressures on the output side of the cells, a first output pressure equalizer is provided. For equalizing the pressures on the input side of the cells, an input pressure equalizer is provided. A disadvantage of this arrangement is that, although pressures can be corrected with the pressure equalizers, it is not possible to define the pressure which is applied to the pumps conveying the dialysate. In addition, it proved to be disadvantageous that the pressure equalizers cause strong vibrations and high noise emission. This may, on the one hand, negatively influence the mode of operation of the dialysis machine and, on the other hand, it may be unpleasant for a patient treated with said dialysis machine.

SUMMARY OF THE INVENTION

Against the background of this prior art, it is an object of the present invention to provide a valve with which pressure equalization can be accomplished in a dialysis machine, while achieving with the aid of simple means low noise emission and/or little vibrations when the machine is in operation. In addition, it is an object of the present invention to provide a dialysis machine with a valve exhibiting high precision with respect to an amount of dialysate supplied to and discharged from a dialyzer.

According to aspects of the present invention, a valve, especially a pressure compensation valve, in particular a pressure follower valve, for a dialysis machine is provided. This valve has a valve housing having formed therein a first flow path for fresh dialysate and a second flow path for exhausted dialysate. A respective flow path is connected to a respective inlet connection and a respective outlet connection. For equalizing or adapting pressures of the flow paths, the valve housing has provided therein an equalizer element. The dialysates of the respective flow paths operatively interact via the equalizer element. The equalizer element is advantageously configured such that vibration and/or noise emission is reduced or comparatively low or prevented. Alternatively or additionally, the equalizer element may have associated therewith a valve seat so as to adjust by means of the equalizer element a size of a flow cross-section of the—especially second—flow path.

It turned out that vibration and noise emission of the valve can be reduced substantially or prevented by simply adapting the valve geometry. Hence, no additional components are required for the purpose of minimizing vibration and noise, but the equalizer element is adapted such that installation space is saved, the solution provided is simple from the device point of view and costs are kept low. The reduction of vibration and noise emission is preferably achieved by optimizing a flow geometry of the equalizer element. If a valve seat is provided, pressure compensation can efficiently be accomplished in a simple manner.

Preferably, the equalizer element is configured and arranged in the valve such that a pressure difference prevailing between the flow paths at the inlet connections is zero or substantially zero at the outlet connections.

The equalizer element is preferably a diaphragm. This diaphragm can be acted upon by fresh dialysate of the first flow path on the one hand and by exhausted dialysate of the second flow path on the other. For reducing or preventing vibration or noise emission, the diaphragm is provided with a diaphragm projection, which is especially covered by dialysate. Through the diaphragm, fresh dialysate and exhausted dialysate can operatively interact within the valve without any direct contact being established, and both flow paths can have the same flow capacity (ml/min).

The diaphragm projection is preferably formed integrally with the diaphragm in a structurally simple manner. The diaphragm consists, e.g., of silicone, which makes it very flexible. In addition, the diaphragm may, e.g., be produced by injection molding in a cost-efficient manner.

Preferably, the diaphragm projection is arranged centrally relative to the diaphragm.

For example, the diaphragm projection is arranged on the diaphragm side of the diaphragm delimiting the second flow path and can thus be acted upon e.g. by exhausted dialysate.

The diaphragm may be configured symmetrically and may especially have an approximately circular circumference. On its circumferential side, the diaphragm may be provided with an annular beading via which it is fixed in position in the valve housing. The beading may additionally serve as a sealing element and can thus fulfil a dual function, namely, fixing the diaphragm in the valve housing and, in addition, sealingly separating the flow paths from one another. Hence, the use of additional sealing elements can be dispensed with in a cost-efficient manner.

According to an advantageous embodiment, one side of the diaphragm, in particular the diaphragm side provided with the diaphragm projection, has formed therein an annular groove, which extends circumferentially around the diaphragm projection. In the area of the annular groove, the diaphragm has a reduced wall thickness, which makes it extremely flexible. When seen in the radial direction of the diaphragm, the annular groove may be formed, e.g., between the diaphragm projection and the beading.

According to a further embodiment of the present invention, the diaphragm delimits, on the side of the second flow path, a fluid chamber or fluid space of the flow path into which a channel section of the second flow path opens. The channel section and the diaphragm are here arranged relative to one another such that the diaphragm projection can be introduced into the channel section. The diaphragm projection thus delimits together with the channel section an annular fluid space through which dialysate can flow. It turned out that this can effectively lead to a reduction of noise and of vibrations.

According to a preferred embodiment, the size of a flow cross-section of the channel section depends on a position of the diaphragm projection, whereby the size of the flow cross-section can be changed through the diaphragm projection. If, for example, the pressure increases in the first flow path and/or decreases in the second flow path, the flow cross-section can be reduced with the diaphragm projection. Vice versa, is it possible to increase the flow cross-section with the diaphragm projection, if the pressure decreases in the first flow path and/or increases in the second flow path.

According to a further development of the present invention, it is imaginable that the second flow path may be completely closed by the diaphragm in the case of certain pressure conditions. The outlet opening of the channel section is, e.g., encompassed by a valve mating surface of the valve seat for the diaphragm. Hence, the valve mating surface defines the valve seat for closing the channel section for the diaphragm. For contacting the valve mating surface, the diaphragm is preferably provided with an annular stop shoulder, which may extend circumferentially around the diaphragm projection. When seen, e.g., in a radial direction, the stop shoulder is formed between the diaphragm projection and the annular groove.

An outlet opening of the channel section of the second flow path is preferably configured to be coaxial with the diaphragm and, consequently, coaxial with the diaphragm projection. When exhausted dialysate in the second flow path flows from the fluid chamber via the outlet opening into the channel section, it turned out that, in combination with the diaphragm, this leads to advantageous flow conditions, which reduce or prevent vibration and/or noise emission of the diaphragm.

It will also be of advantage when the diaphragm projection is configured to be conical or frusto-conical and when it tapers in a direction away from the diaphragm. An end portion of the diaphragm may here additionally be configured to have the shape of a spherical segment. Hence, the diaphragm projection has a rounded top.

The outlet opening of the channel section of the second flow path preferably has an approximately frusto-conical inner circumferential surface, which tapers in a direction away from the diaphragm.

Due to the frusto-conical shape of outer circumferential surface of the diaphragm projection and of the inner circumferential surface of the outlet opening, an annular space is delimited through which the dialysate can flow and the flow cross-section of which can depend on the position of the diaphragm projection. Preferably, an inclination angle of the frusto-conical inner circumferential surface of the outlet opening and an inclination angle of the frusto-conical outer circumferential surface of the diaphragm projection are respectively chosen such that the distance between said surfaces increases in the direction of the diaphragm. Preferably, the frusto-conical inner circumferential surface of the outlet opening extends from the from the valve mating surface. If the valve mating surface is encompassed by a frusto-conical circumferential surface which increases in width in a direction away from the diaphragm, this will lead to a precise definition of the valve mating surface.

According to a further development of the present invention, the channel section ends with its outlet opening in the form of a protrusion within the fluid chamber and defines an annular space therein. This is of great advantage under the aspect of fluidics. The annular space is e.g. approximately rotationally symmetric, and the longitudinal axis of said annular space may extend approximately coaxially with the longitudinal axis of the channel section and/or the longitudinal axis of the diaphragm. Preferably, the channel section communicates with the second outlet connection and the fluid space communicates with the second inlet connection. The second inlet connection communicates with the fluid chamber via a connection channel which opens substantially into the fluid chamber. The connection channel opens preferably radially or tangentially into the fluid space and extends preferably at a maximum distance from the diaphragm.

A bypass channel may branch off from the second flow path, in particular from the fluid chamber or from a point upstream of the fluid chamber (e.g. from the connection channel). This bypass channel communicates e.g. with a bypass connection of the valve housing. Said bypass channel is especially necessary, if a substitution or an online infusion bolus injection is provided in the case of the dialysis machine. The bypass connection may have connected thereto a bypass valve. The latter is preferably connected directly to the valve housing and may thus define a unit therewith. The bypass valve may e.g. be used for controlling the bypass channel to be open or closed. A valve element of the bypass valve is here actuable especially via an electromagnetic actuator.

Preferably, also the first flow path comprises a fluid chamber, which is delimited by a diaphragm side of the diaphragm.

According to a preferred embodiment, the valve housing comprises two housing parts, the diaphragm being arranged between these housing parts. The first housing part may be configured as an upper shell and the second housing part may include the valve seat and the valve mating surface, respectively. The respective housing parts have each formed therein a flow path in an advantageous manner. The housing parts may jointly define an annular beading accommodation space into which the beading of the diaphragm can be inserted.

According to a structurally simple embodiment, the first flow path may be formed in the first housing part simply as a substantially straight channel section or channel bore, the channel section extending through the full valve housing and being connected to the first inlet connection on the one hand and to the first outlet connection on the other. The fluid chamber, which is delimited by the diaphragm, may be formed radially to the channel section. It follows that, when the housing part is being produced, the fluid chamber can simply be formed from a lateral surface of the housing part into said lateral surface. Starting, e.g., from the channel section of the first flow path, the fluid chamber is configured to have the shape of a circular cylinder or of a cylinder. A fluid-chamber end section which is remote from the channel section preferably has a frusto-conical inner circumferential surface that increases in width towards the diaphragm. Preferably, a maximum diameter of the fluid chamber of the first flow path corresponds to a maximum diameter of the fluid chamber of the second flow path, the fluid chambers being arranged coaxially with one another. The diaphragm arranged therebetween can thus easily have identically dimensioned pressure application surfaces on both sides.

For connecting the housing parts, one of the housing parts may be provided with a housing projection which is introduced in a housing recess of the other housing part. Preferably the housing projection has an outer circumferential surface whose cross-section has substantially the shape of a cylinder or a circular cylinder. In addition, the fluid chamber of the first flow path or, alternatively, of the second flow path may extend through the housing projection, in particular coaxially therewith. Hence, the projection is annular in shape. An inner circumferential surface of the housing recess is then adapted to the housing projection and has, consequently, a cylindrical or circular-cylindrical cross-section as well. According to a further development, an annuar end face of the housing projection and an annular bottom area of the housing recess are each provided with an annular groove, said annular grooves delimiting together the beading accommodation space. The beading of the diaphragm inserted therein can then easily also fulfil the function of a sealing ring.

The connections of the flow paths are preferably configured as hose sockets, which are screwed to the valve housing.

According to aspects of the present invention, a dialysis machine with a valve according to one of the above aspects is provided. The dialysis machine may comprise a pump with which fresh dialysate can be conveyed from a dialysate source to a dialyzer via a balancing unit. Making use of the same or an additional pump, the exhausted dialysate is conveyable from the dialyzer via the balancing unit to a dialyzer sink. Preferably, the first flow path of the valve communicates with a flow path with the fresh dialysate and the second flow path of the valve communicates with a flow path with the exhausted dialysate.

This solution has the advantage that a change of pressures in the flow paths can be compensated for by the valve and that, consequently, an ultrafiltration volume predetermined by the balancing unit will remain substantially equal. Hence, the amount of dialysate discharged from the balancing unit is equal to the amount of recirculated dialysate. If the pressure difference were not compensated, a balance of the balancing unit could—due to a change in an expansion of the components of the dialysis machine—lie outside an admissible tolerance limit from a predetermined pressure difference between the flow paths with the fresh dialysate and the exhausted dialysate onwards.

According to a further development of the present invention, the first flow path of the valve may, between the balancing unit and the dialyzer, be in fluid communication with the flow path with the fresh dialysate. The second flow path of the fluid is, between the balancing unit and the pressure medium sink, preferably in fluid communication with the flow path with the exhausted dialysate.

Downstream of the valve in the flow path with the fresh dialysate, a (first) constant pressure valve may be arranged. Additionally or alternatively, a (second) constant pressure valve may be provided downstream of the valve in the flow path with the exhausted dialysate. The use of the constant pressure valves has the effect that constant pressure conditions prevail. The combination of one or of both constant pressure valves with the valve according to the present invention has the effect that a constant pressure or pilot pressure can be adjusted for the pump or the pumps, whereby the ultrafiltration accuracy will be increased.

The first pump is preferably arranged upstream of the balancing unit in the flow path with the fresh dialysate and the second pump is fluidically arranged between the balancing unit and the dialyzer in the flow path with the exhausted dialysate. The first constant pressure valve may then be provided in the flow path of the fresh dialysate between the valve and the dialyzer and the second constant pressure valve may be provided in the flow path of the exhausted dialysate downstream of the valve. In the flow path with the fresh dialysate, a dialysate filter can be provided between the first constant pressure valve and the valve.

According to a further development of the present invention, the ultrafiltration volume can be measured and controlled via the balancing unit and the ultrafiltration pump. The ultrafiltration pump is, on the input side, connected preferably between the second pump and the balancing unit and, on the output side, preferably between the balancing unit and the valve (or alternatively downstream of the valve), i.e. a dialysate conveyed by the ultrafiltration pump bypasses the balancing unit.

The balancing unit comprises preferably a balancing chamber with two cells, which can be separated from one another by a diaphragm. One of said cells is here preferably connected to the flow path with the fresh dialysate and the other cell is preferably connected to the flow path with the exhausted dialysate. It will be advantageous to provide two balancing chambers which each comprise two cells. Charging and discharging dialysate can be controlled via switching valves in the case of one or a plurality of balancing chambers, said valves being especially electromagnetically actuable.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
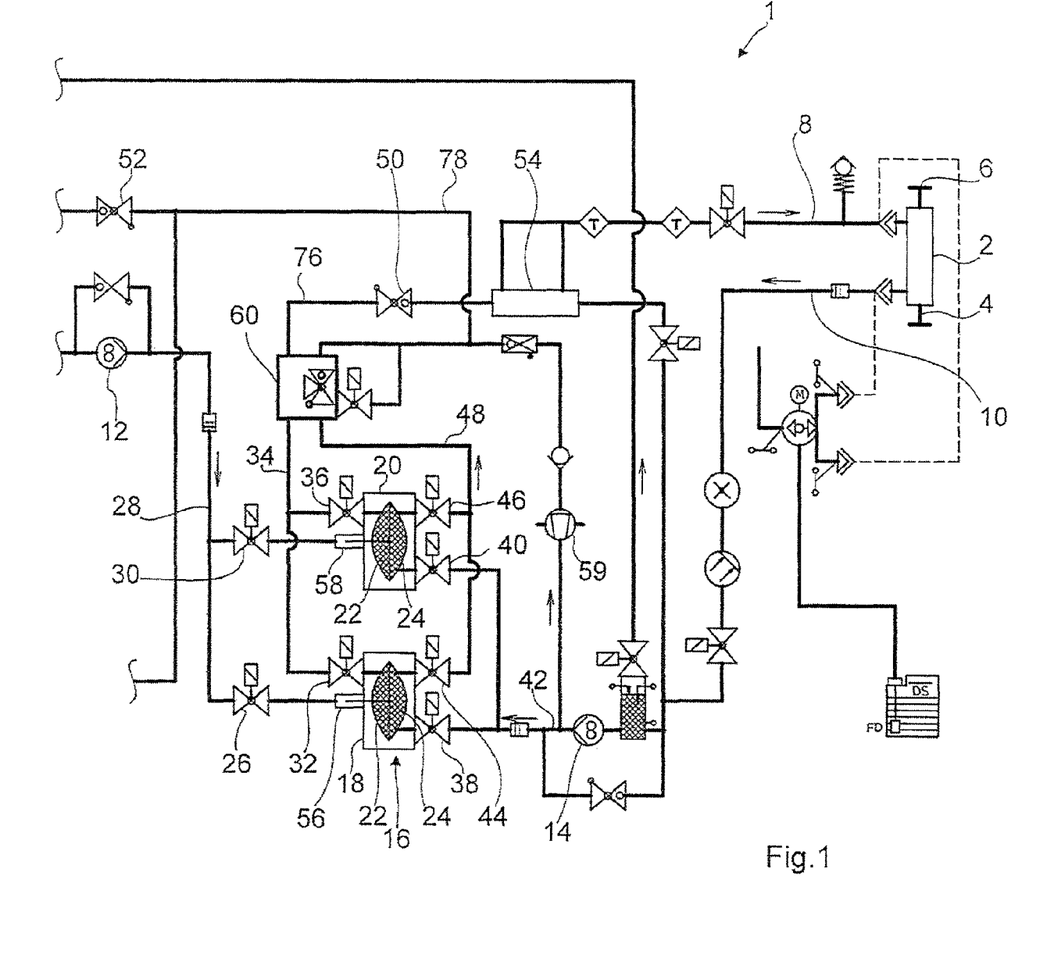
FIG. 1 shows a circuit diagram of an embodiment of a dialysis machine according to aspects of the present invention.

According to FIG. 1, a dialysis machine 1 with a dialyzer 2 is shown. Since the basic structural design of the dialysis machine 1 is known to a sufficient extent, only that which is essential to the present invention will be explained in the following.

The dialysis machine 1 is used for cleaning a patient's blood, which is supplied to the dialyzer 2 via a blood supply line 4 and discharged from the dialyzer 2 via a blood discharge line 6. Fresh dialysate is supplied to the dialyzer 2 via a supply line 8 and exhausted dialysate is discharged therefrom via a discharge line 10. For conveying the dialysate to the dialyzer 2, a first pump 12 (flux pump) is provided. This pump conveys a dialysate from a dialysate source, not shown, via the supply line 8 to the dialyzer 2. For discharging the exhausted dialysate from the dialyzer 2, a second pump 14 (flux pump) is provided. The pumps 12 and 14 are configured, e.g., as gear pumps. In the flow path comprising the fresh dialysate, a balancing unit 16 is provided between the first pump 12 and the dialyzer 2. Said balancing unit 16 is additionally switched into the flow path comprising the exhausted dialysate between the second pump 14 and a pressure medium sink, which is not shown in FIG. 1.

The balancing unit 16 comprises a first balancing chamber 18 and a second balancing chamber 20. The balancing chambers 18 and 20 each comprise first and second cells 22 and 24, which are separated via a diaphragm. The balancing chambers 18 and 20 are configured identically. The diaphragm provided therein is deflectable to both sides in a flexible manner. The first cell 22 of the first balancing chamber 18 communicates with a pump line 28 via first switching valve 26, the output side of said pump line 28 being connected to the first pump 12. The same applies to the first cell 22 of the second balancing chamber 20, which communicates with the pump line 28 via a second switching valve 30. The output side of the first cell 22 of the first balancing chamber 18 communicates with a supply line 34 via a switching valve 32, said supply line 34 having also connected thereto the first cell 22 of the second balancing chamber 20 via a switching valve 36. The first cells 22 thus communicate with the flow path with fresh dialysate. The second cells 24 of the balancing chambers 18 and 20, however, communicate with the flow path with exhausted dialysate. To this end, a respective second cell 24 communicates with a pump line 42 via a switching valve 38 and 40, respectively, the output side of said pump line 42 being connected to the second pump 14. A respective switching valve 44, 46 connects a respective second cell 24 to a discharge line 48 leading to the dialysate sink. The switching valves 30, 32, 36, 38, 40, 44, 46 are electromagnetically actuable.

In the following, the mode of operation of the balancing unit 16 will be explained. Initially (prior to starting the treatment), the speeds of the pumps 12 and 14 are adapted to one another so as to first guarantee that the diaphragms of the balancing chambers 18 and 20 are synchronized. In a first step, the switching valves 26, 36, 40, 44 are controlled to be open and the switching valves 30, 32, 38, 46 are controlled to be closed. Hence, fresh dialysate flows from the first pump 12 into the first cell 22 of the first balancing chamber 18 and displaces exhausted dialysate into the dialysate sink via the diaphragm arranged in said balancing chamber 18. Simultaneously, exhausted dialysate flows from the pump 14 into the second cell 24 of the second balancing chamber 20 thus displacing fresh dialysate in the first cell 22 towards the dialyzer 2. In the next step, all the switching valves 30, 32, 36, 38, 40, 44, 46 are closed. Subsequently, in the following step, the switching valves 30, 32, 38, 46 are controlled to be open and the switching valves 26, 36, 40, 44 are controlled to be closed. Hence, fresh dialysate flows from the first pump 12 into the first cell 22 of the second balancing chamber 20 and displaces exhausted dialysate in the second cell 24 via the discharge line 48 into the dialysate sink. Simultaneously, exhausted dialysate flows from the second pump 14 into the second cell 24 of the first balancing chamber 18 and displaces fresh dialysate towards the dialyzer 2. Subsequently, all the switching valves 30, 32, 36, 38, 40, 44, 46 are closed and the steps are carried out repeatedly.

In order to keep a pressure constant between the balancing unit 16 and the dialyzer 2 in the flow path with the fresh dialysate, a constant pressure valve 50 is provided. Another constant pressure valve 52 is provided in the flow path with the exhausted dialysate downstream of the balancing unit 16. For filtering the fresh dialysate, the balancing unit 16 and the dialyzer 2 have additionally provided between them a dialysate filter 54. The latter is especially provided downstream of the constant pressure valve 50.

A position of the diaphragm of a respective balancing chamber 18 is detectable via a respective inductive diaphragm position sensor 56, 58. A respective diaphragm position sensor 56, 58 is here connected to a respective diaphragm and comprises a sensor element that is movable in a coil for inductive position detection.

Via an ultrafiltration pump 59, a part of the exhausted dialysate can be branched off between the second pump 14 and the balancing unit 16 and, bypassing the balancing unit 16, it can be conveyed to the dialysate sink. The amount of fluid discharged here corresponds e.g. to the amount of fluid transferred from the blood into the dialysate in the dialyzer 2.

The constant pressure valves 50, 52 are used for causing the pumps 12 and 14 to move the diaphragms of the balancing chambers 18 and 20 against defined flow resistances and for rendering the counterpressures in the two balancing chambers 18 and 20 identical. If the speeds of the pumps 12 and 14 are changed so as to change a volume flow of the dialysate, this will in particular also have the effect that a flow resistance of the dialysate filter 54 changes. This means that, if the adjustment of the constant pressure valves 50 and 52 does not change, there will be a change in the counterpressures of the balancing chambers 18 and 20. Due to the changing pressures, also the expansion of the lines and tubes of the dialysis machine and of the components of the balancing unit 16 will change, i.e. the balance of the dialysate of the balancing unit 16 is pressure dependent. The counterpressures of the two balancing chambers 18 and 20 may also change due to clogging of the dialysate filter 54.

The change in the counterpressures of the balancing chambers 18 and 20 in the case of different operating conditions may lead to substantial deviations of the ultrafiltration volumes. For compensating the pressure differences between the flow path with the fresh dialysate (dialysate supply) and the flow path with the exhausted dialysate (dialysate recirculation), the valve or pressure compensation valve 60 according to the present invention is provided. This pressure compensation valve is connected to the flow path with the fresh dialysate between the balancing unit 16 and the constant pressure valve 50 on the one hand and to the flow path with the exhausted dialysate between the balancing unit 16 and the constant pressure valve 52 on the other.

Figure 2:
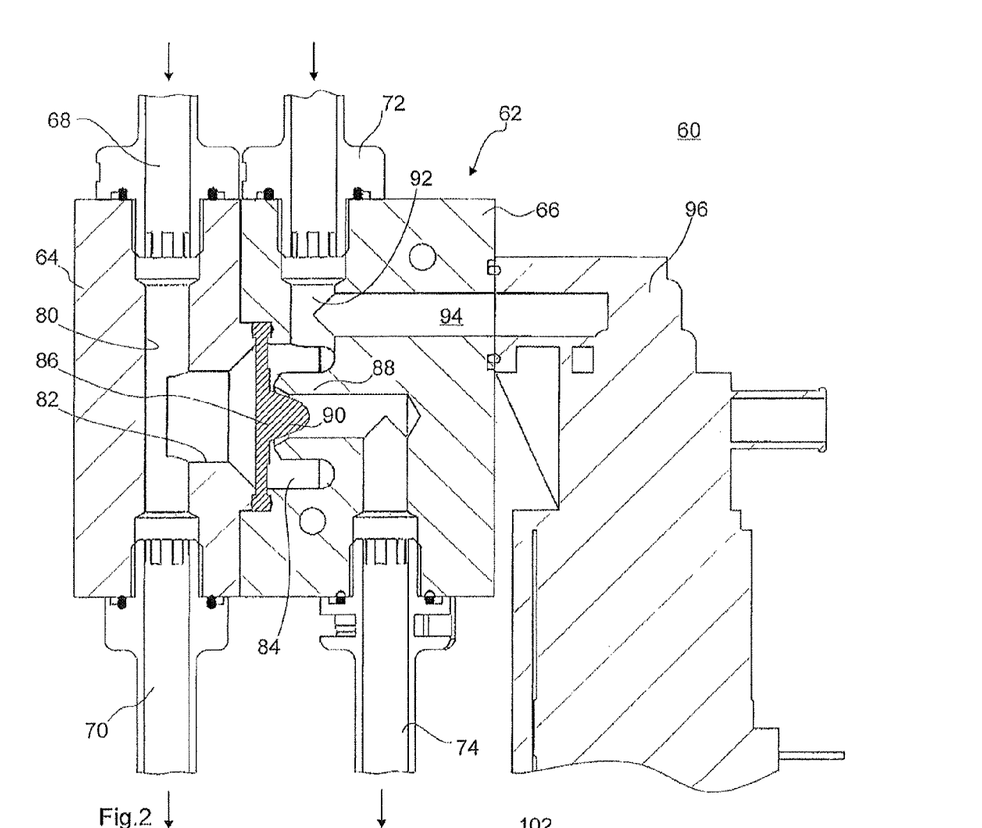
FIG. 2 shows a cross-section of a valve according to the present invention, said valve belonging to said embodiment of the dialysis machine.

According to FIG. 2, the pressure compensation valve 60 is shown, which comprises a first housing part 64 and a second housing part 66. The first housing part 64 has a first inlet connection 68 and a first outlet connection 70. The second housing part 66 has a second inlet connection 72 and a second outlet connection 74. The connections 68 to 74 are configured as hose sockets, which are screwed to the valve housing 62. The first inlet connection 68 is connected to the supply line 34, see also FIG. 1. The outlet connection 70 is connected to the constant pressure valve 50 via an intermediate line 76. The inlet connection 72, however, is connected to the discharge line 48, and the outlet connection 74 is connected to the second constant pressure valve 52 via an intermediate line 78. Thus, the first valve housing 62 has formed therein a first flow path for the fresh dialysate and the second housing part 66 has formed therein a second flow path for the exhausted dialysate. For forming the first flow path, the first housing part 64 has formed therein a bore 80 that extends therethrough. Radially to said bore, a fluid chamber 82 is formed in the first housing part 64, said fluid chamber 82 extending towards the second housing part 66. Also said second housing part 66 is provided with a fluid chamber 84, which extends from said fluid chamber 82. The fluid chambers 82, 84 are here fluidically separated from one another by an equalizer element in the form of a diaphragm 86. The diaphragm 86 is fixed in position between the housing parts 64 and 66. A channel section 88 opens into the fluid chamber 84 approximately coaxially with the diaphragm 86. This channel section 88 projects partially into the fluid chamber 84 and defines therein an annular space. The diaphragm 86 protrudes into the channel section 88 with a conical diaphragm projection 90. The channel section 88 is defined by a blind hole bore into which an additional blind hole bore opens, approximately radially thereto, which is connected to the second outlet connection 74. A bore 92, which is connected to the second inlet connection 72, opens radially into the fluid chamber 84. A bypass channel in the form of a bore 94 branches off from said bore 92, said bore 94 being formed into the second housing part 66 from outside and used for connecting a bypass valve 96 thereto. Exhausted dialysate thus flows via the second inlet connection 72 and the bore 92 into the fluid chamber 84 and from said fluid chamber 84 via the channel section 88 to the second outlet connection 74.

Figure 3:
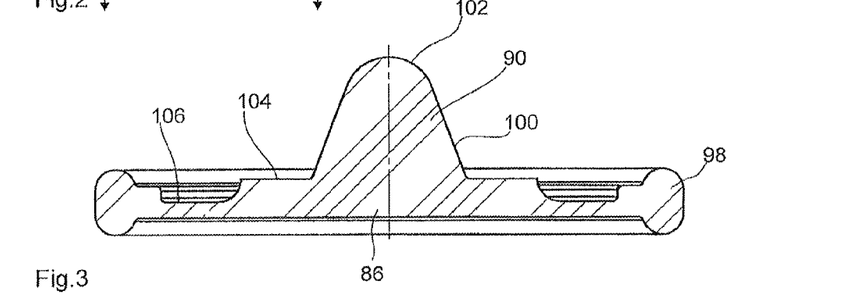
FIG. 3 shows a cross-section of an equalizer element of the valve, FIGS. 4*a* and 4*b* each show a cross-section of a housing part of the valve.

According to FIG. 3, the diaphragm 86 is configured in a rotationally symmetric manner such that its cross-section has approximately the shape of a circular cylinder. On its circumferential side, it is provided with a beading 98 through which it is adapted to be fixed in position between the housing parts 64 and 66 and which additionally serves as a sealing element. The diaphragm projection 90 is formed coaxially with the diaphragm 86 and has a frusto-conical outer circumferential surface 100 and a rounded end face 102. When seen in a radial direction, the diaphragm projection 90 is followed by an annular surface as a stop shoulder 104, which can be brought into contact with the channel section 88 on the end-face side thereof, see also FIG. 2, for closing the channel section 88, as will be explained in more detail hereinbelow. The stop shoulder 104 is followed, when seen in a radial direction, by an annular groove 106 through which a wall thickness of the diaphragm 86 is reduced so as to provide an increase in flexibility.

Figure 4A:
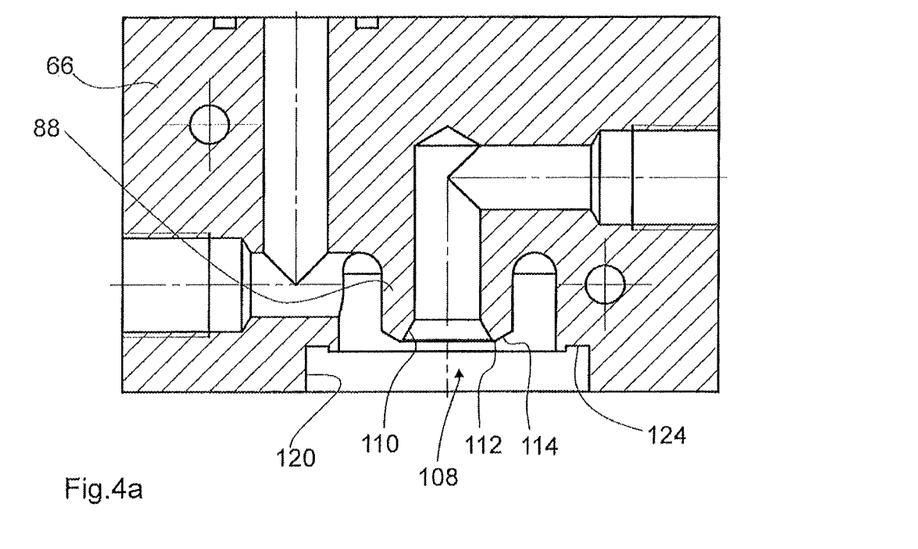

According to FIG. 4a, the channel section 88 of the first housing part 64 has an outlet opening 108 with a frusto-conical inner circumferential surface 110 tapering in a direction away from the diaphragm 86, see FIG. 2. On the end-face side of the channel section 88, the outlet opening 108 is followed by an annular valve mating surface 112 with which the diaphragm 86 can be brought into contact via its stop shoulder 104, see FIG. 3. The circumferential surface 114 following the valve mating surface in a radial direction is frusto-conical in shape and widens in a direction away from the diaphragm 86, see FIG. 2.

Figure 4B:
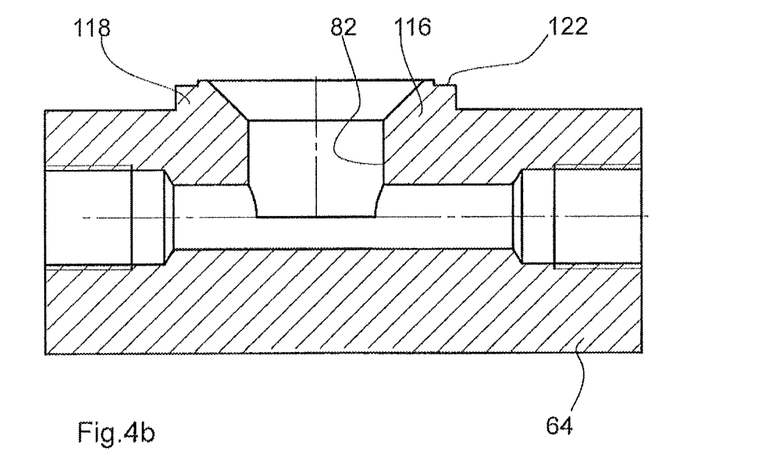

According to FIG. 4b, the fluid chamber 82 of the first housing part 64 is configured as a radial bore and has a diameter which is approximately twice as large as that of the bore 80, see FIG. 2. In the direction of the second housing part 66, the fluid chamber 82 increases in width with a frusto-conical inner circumferential surface 116. The first housing part 64 additionally has a housing projection 118 whose cross-section has approximately the shape of a circular cylinder, the fluid chamber 82 extending through said housing projection 118 coaxially therewith. In the assembled condition of the housing parts 64 and 66, this housing projection 118 projects into a housing recess 120 of the second housing part 66. On the end-face side of the housing projection 118, an annular groove 122 is formed. In addition, a further annular groove 124 is formed on the bottom side of the housing recess 120. These annular grooves define together a beading accommodation space for the beading 98 of the diaphragm 86, see FIG. 3. In the assembled condition of the housing parts 64 and 66, the end face of the housing projection 118 is spaced apart from the bottom surface of the housing recess 120, and an annular gap is defined therebetween. The diaphragm 86 extends through said annular gap to the outside of said beading accommodation space.

In the assembled condition of the housing parts 64 and 66, said housing parts are preferably screwed together. Also the bypass valve 96 is preferably screwed to the valve housing 62.

In the following, the mode of operation of the pressure compensation valve 60 will be explained in more detail making reference to FIGS. 2 to 4b. If there is an increase in pressure in the first flow path of the first housing part 64, the diaphragm 86 according to FIG. 2 will be deflected from the neutral position shown in said FIG. 2 towards the channel section 88. This has the effect that, on the one hand, the diaphragm projection 90 moves deeper into the channel section 88 and that, on the other hand, the stop shoulder 104, see FIG. 3, approaches the valve mating surface 112. This leads to a narrowing of the flow cross-section of the second flow path in the second housing part 66, whereby an increase in pressure is caused on the inlet side of the second housing part 66 and, consequently, according to FIG. 1, on the outlet side of the balancing unit 16 in the flow path of the exhausted dialysate. If the pressure decreases in the first flow path of the first housing part 64, the diaphragm 86 will be moved in the opposite direction and a corresponding adaptation of pressure will occur in the second flow path.

The combination of the constant pressure valves 50, 52 with the pressure compensation valve 60 allows a constant pressure (pilot pressure) to be adjusted for the pumps 12 and 14 and the ultrafiltration pump 59. This leads to an improved ultrafiltration accuracy as well as an improved substitution accuracy and a more precise online infusion bolus injection—especially due to the constant pressure valve 50—since the hose pump used for this purpose (not shown) will operate with higher accuracy, when the pressure in the first flow path with the fresh dialysate is kept in a positive range. Positive range means that the pressure is higher than 0 on the input side. However, the pressure level established e.g. in the case of the dialysis machine according to the above explained reference EP 0 597 817 is, due to pressure compensation with two pressure compensation valves, determined by the flow resistances in the dialysate circuit and results therefore, in a disadvantageous manner, not necessarily in a constant positive pressure. Pressure differences between the inlet connections 68 and 72 of the pressure compensation valve 60 according to FIG. 2, which are measurable upstream of the pressure compensation valve, no longer exist when the dialysate has flown through the fluid chambers 82 and 84.

Fluttering and vibrating of the diaphragm 86 is fully eliminated by the frusto-conical shape of the diaphragm projection 90 and the advantageous incident flow on the diaphragm 86.

The use of the pressure compensation valve 60 makes a calibration of the constant pressure valves 50 and 52 superfluous.

Due to the adaptation of the pressure differences through the pressure compensation valve 60, a greater expansion of the balancing chambers 18 and 20 is acceptable, without any deterioration of the ultrafiltration accuracy occurring. The balancing chambers 18 and 20 may therefore be made of a softer material and/or they may be thinner and/or have less braces. The components of the dialysis machine acted upon by pressure may, furthermore, also be cost-efficient injection molded parts. In addition, the lines of the dialysis machine 1 may consist of cost-efficient, comparatively thin-walled silicone hoses having a wall thickness of e.g. 2 to 2.5 mm. Up to now, silicone hoses used for a dialysis machine normally have had a wall thickness of 3 mm.

Alternatively to the cost-intensive constant pressure valves 50 and 52, it is also imaginable to provide mechanically produced throttling points, e.g., a restriction or a reduction of diameter in a bore or in a hose.

Figure 5:
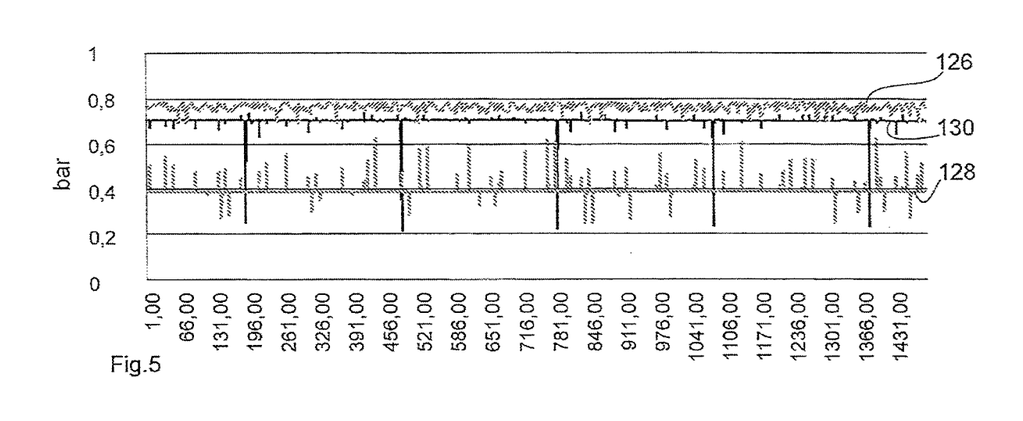
FIG. 5 shows a comparison of pressure differences of the dialysis machine according to aspects of the present invention in comparison with the prior art.

According to FIG. 5, a pressure difference 126 of the dialysis machine 1 according to the present invention between the flow path with the exhausted dialysate and the flow path with the fresh dialysate is plotted against time. It can be seen that the pressure difference 126 exhibits minor fluctuations.

In the case of a pressure difference 128 of a dialysis machine according to the prior art large fluctuations can, however, be seen. In addition, an adjusted resistance coefficient 130 can be seen in FIG. 5.

Figure 6A:
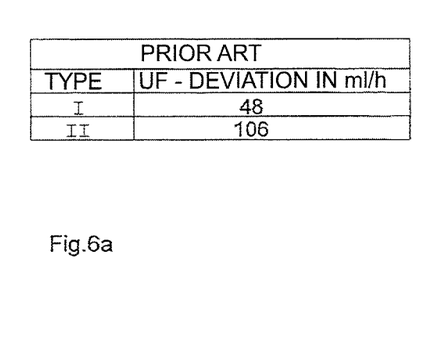
FIGS. 6*a* and 6*b* show a comparison of the deviations occurring in the case of an ultrafiltration volume in the dialysis machine according to aspects of the present invention and in the prior art.
Figure 6B:
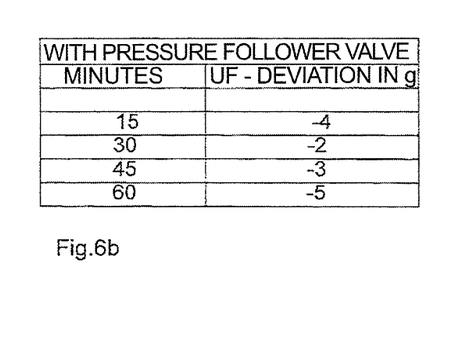

The table according to FIG. 6a shows average values indicated for the mean ultrafiltration volume—(UF)—deviation (ml/hour) in data sheets of known machines (type I and type II). According to these values, known dialysis machines exhibit a comparatively high deviation of the ultrafiltration volume with increasing operating times, whereas according to FIG. 6b the ultrafiltration volume remains substantially constant over the operating time in the case of the dialysis machine 1 according to the present invention.

The present invention discloses a pressure compensation valve for a dialysis machine. Said pressure compensation valve has a valve housing, in which a flow path with fresh dialysate is separated from a flow path with exhausted dialysate with a diaphragm. The diaphragm and the valve housing are here configured such that pressure compensation is possible. In addition, the diaphragm is configured such that, during operation, no vibrations or a reduced amount of vibrations and/or no noise emission or a reduced amount of noise emission will occur.

In addition, a dialysis machine comprising such a pressure compensation valve is disclosed. Said dialysis machine comprises a balancing unit, the pressure compensation valve being arranged on the outlet side of the balancing unit.

The invention claimed is:

1. A valve for a dialysis machine, comprising:
a valve housing having formed therein a first flow path in fluid communication with a first respective inlet connection and a first respective outlet connection and a second flow path, separate from the first flow path, the second flow path in fluid communication with a second respective inlet connection and a second respective outlet connection, and
an equalizer element arranged within the valve housing and configured to separate the first flow path from the second flow path, wherein the equalizer element equalizes pressures of the flow paths and through which equalizer element the fluids of respective flow paths operatively interact without direct contact, the equalizer element having associated therewith a valve seat.

2. The valve according to claim 1, wherein the equalizer element is a diaphragm, which is acted upon by the fluid of the first flow path and by the fluid of the second flow path and which is provided with a diaphragm projection.

3. The valve according to claim 2, wherein the diaphragm is configured as a sealing element for fluidically separating the first and second flow paths.

4. The valve according to claim 2, wherein the first flow path comprises a fluid chamber, which is delimited by the diaphragm.

5. The valve according to claim 2, wherein the valve housing is configured such that it comprises two housing parts, and the diaphragm is arranged between the two housing parts.

6. The valve according to claim 5, wherein, for connecting the housing parts, one housing part is provided with a housing projection, which is introduced in a housing recess of the other housing part.

7. The valve according to claim 1, wherein the equalizer element is configured such that vibration and/or noise emission will be reduced.

8. A valve for a dialysis machine, comprising:
a valve housing having formed therein a first flow path in fluid communication with a first inlet connection and a first outlet connection and a second flow path in fluid communication with a second inlet connection and a second outlet connection; and
an equalizer element arranged within the valve housing that equalizes pressures of the flow paths and through which the fluids of respective flow paths operatively interact, the equalizer element having associated therewith a valve seat;
wherein the equalizer element is a diaphragm, which is acted upon by the fluid of the first flow path and by the fluid of the second flow path and which is provided with a diaphragm projection, and
wherein the second flow path comprises a fluid space into which a channel section of the second flow path opens, the diaphragm projection being adapted to be introduced into said channel section.

9. The valve according to claim 8, wherein an outlet opening of the channel section is provided with a valve mating surface to define the valve seat.

10. The valve according to claim 9, wherein the diaphragm has a stop shoulder for contacting the valve mating surface.

11. The valve according to claim 8, wherein the diaphragm projection is configured to be conical or frustoconical in shape and tapers in a direction away from the diaphragm.

12. The valve according to claim 8, wherein the channel section ends in the form of a protrusion within the fluid chamber and defines an annular space therein.

13. The valve according to claim 8, further comprising:
a bypass channel for connection to a bypass valve that branches off from the second flow path in the second housing part.

* * * * *